Figure 1:
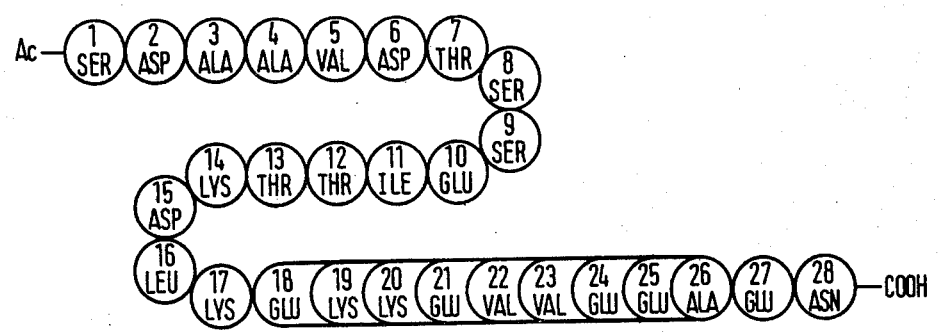

United States Patent [19]

Birr et al.

[11] Patent Number: 4,470,926

[45] Date of Patent: Sep. 11, 1984

[54] MEDICAMENTS CONTAINING THYMOSIN ALPHA 1 FRAGMENTS AND HAVING AN IMMUNOSTIMULANT ACTION, AND FRAGMENTS OF THYMOSIN ALPHA 1

[75] Inventors: Christian Birr, Leimen; Ulrich Stollenwerk; Ilona Werner, both of Heidelberg, all of Fed. Rep. of Germany

[73] Assignee: Max-Planck-Gesellschaft zur Förderung der Wissenschaften e.V., Gottingen, Fed. Rep. of Germany

[21] Appl. No.: 133,708

[22] Filed: Mar. 25, 1980

[30] Foreign Application Priority Data

Jan. 18, 1980 [DE] Fed. Rep. of Germany ....... 3001775

[51] Int. Cl.$^3$ ............................................. C07C 103/52
[52] U.S. Cl. ............................................. 260/112.5 R
[58] Field of Search ................................. 260/112.5 R

[56] References Cited

U.S. PATENT DOCUMENTS 4,148,788 4/1979 Wang .......................... 260/112.5 R

OTHER PUBLICATIONS

Pettit, Synthetic Peptides, (1971), 106–107.
Abiko, et al., Chem. Pharm. Bull. 27, 3171–3175.
Birr, et al., Angew. Chem. Int. Ed. Engl. 18, (1979), 394–395.

*Primary Examiner*—Delbert R. Phillips
*Attorney, Agent, or Firm*—Felfe & Lynch

[57] ABSTRACT

The Thymosin alpha 1 fragment compound Glu-Ala-Glu-Asn-OH.

1 Claim, 10 Drawing Figures

Thymosin α₁

FRAGMENT-Ia

FRAGMENT-II

FRAGMENT - III

FRAGMENT-IY

FRAGMENT-V

FRAGMENT - VI

FRAGMENT-VII

FRAGMENT-IVa

MEDICAMENTS CONTAINING THYMOSIN ALPHA 1 FRAGMENTS AND HAVING AN IMMUNOSTIMULANT ACTION, AND FRAGMENTS OF THYMOSIN ALPHA 1

DESCRIPTION

The invention relates to medicaments with immunostimulating or immunoregulating action, which can be used for the treatment of immunity deficiency diseases, of virus infections, of accelerated aging, treatment for probable tumor formation and especially the treatment of cancer, and also thymosin $\alpha_1$ fragments which are contained as active substance in this medicament.

The influencing of the immune apparatus of the body by polypeptides of the thymus gland has recently been studied with great interest and growing success. This is a consequence of the discovery that cell-free protein extracts of the thymus gland of calves, such as the standard preparation of what is known as "thymosin fraction No. 5," suppress to various extents immune deficiency diseases such as a poor rejection of transplants, an increased sensitivity to infection, accelerated aging, and increased probability of the occurrence of tumors. Recently it was reported that the clinical use of thymosin fraction No. 5 on patients suffering from leukemia and other types of cancer has resulted in healing effects, especially in the case of lung cancer (P. B. Chretien et al, J. D. Cancer Treat. Rep. 62 (1978) 1787-1790).

In 1977, A. L. Goldstein et al. (J. Proc. Natl. Acad. Sci, USA, 74 (1977) 725) succeeded in separating an acid component in pure form from the thymosin polypeptide mixture, and called it thymosin $\alpha_1$; they also gave its peptide sequence. With 28 amino acids, thymosin $\alpha_1$ has a molecular weight of 3107 and with nine acid side functions and only four basic groups, it has an acid reaction. Thymosin $\alpha_1$ has the amino acid sequence and secondary structure represented in FIG. 1 (Ac represents the acetyl group).

Since thymosin $\alpha_1$ is very difficult to separate from thymus glands, a method for its total synthesis has been described (J. A. C. S. 101, 1 (1979) 253-254). The applicant's previous patent application No. P 29 19 592.4 also relates to such a method for the preparation of thymosin and derivatives thereof.

It has now been found that even fragments of thymosin $\alpha_1$ exercise the same immunoregulating or immunostimulating actions as thymosin $\alpha_1$, although to a lesser extent. Thus, certain thymosin $\alpha_1$ fragments, which are the subject of the present invention, can be used for the treatment of immune deficiency diseases, such as T-cell deficiency states, accelerated aging, the elevated probability of tumor formation, and especially cancer. The slight disadvantage of the slightly weaker action of the thymosin $\alpha_1$ fragments of the invention as compared with thymosin $\alpha_1$ is more than compensated by the fact that these fragments can be prepared more simply, with higher yields and in better purity, thereby making possible the clinical application of these thymosin $\alpha_1$ fragments.

The subject matter of the invention, therefore, is medicaments having an immunostimulating action, which contain as active substance at least one thymosin $\alpha_1$ fragment and/or at least one derivative thereof in free form or in the form of a pharmacologically acceptable salt. This medicament of the invention can also contain two or more of the thymosin $\alpha_1$ fragments defined hereinafter, and contains, in addition to the active substances, conventional, pharmacologically acceptable binding agents, carrier materials and/or adjuvants suitable for the selected method of administration.

The thymosin $\alpha_1$ fragments which are contained as active substances in the medicament of the invention, and which are also subject matter of the present invention, are the following:

| Fragment I: | 1 2 3 4 5 6 |
| | Ser—Asp—Ala—Ala—Val—Asp |

| Fragment Ia: | 1 2 3 4 5 6 |
| | Lys—asp—Ala—Ala—Val—Asp |

| Fragment II: | 7 8 9 10 11 12 |
| | Thr—ser—Ser—Glu—Ile—Thr |

| Fragment III: | 13 14 15 16 17 18 19 |
| | Thr—Lys—Asp—Leu—Lys—Glu—Lys |

| Fragment IV: | 20 21 22 23 24 |
| | Lys—Glu—Val—Val—Glu |

| Fragment IVa: | 20 21 22 23 24 |
| | Lys—Glu—Val—Val—Gla |

| Fragment V: | 25 26 27 28 |
| | Glu—Ala—Glu—Asn |

| Fragment Va: | 25 26 27 28 |
| | Gla—Ala—Glu—Asn |

| Fragment VI: | 20 21 22 23 24 25 26 27 28 |
| | Lys—Glu—Val—Val—Glu—Glu—Ala—Glu—Asn |

| Fragment VIa: | 20 21 22 23 24 25 26 27 28 |
| | Lys—Glu—Val—Val—Gla—Gla—Ala—Glu—Asn |

| Fragment VII: | 13 14 15 16 17 18 19 20 21 22 23 24 25 26 27 28 |
| | Thr—Lys—Asp—Leu—Lys—Glu—Lys—Lys—Glu—Val—Val—Glu—Glu—Ala—Glu—Asn |

Fragment VIII:

-continued

| 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|
| Thr | Ser | Ser | Glu | Ile | Thr | Thr | Lys | Asp | Leu | Lys | Glu | Lys | Lys | Glu | Val | Val | Glu | Glu | Ala | Glu | Asn |

Fragment IX:

| 1 | 2 | 3 | 4 | 5 | 6 | 7 | 8 | 9 | 10 | 11 | 12 |
|---|---|---|---|---|---|---|---|---|---|---|---|
| Ac—Ser | Asp | Ala | Ala | Val | Asp | Thr | Ser | Ser | Glu | Ile | Thr |

The above-given fragments I to IX in accordance with the invention can bear at their N-terminus an acyl group having 1 to 6 carbon atoms, especially an acetyl group or an acyl glycine group whose acyl residue can have 1 to 6 carbon atoms. At the same time, in the corresponding thymosin $\alpha_1$ fragments the glutamic acid residues 10, 21, 24, 25 and 27 as well as the aspartic acid residue 15 and the asparagine residue 28 can be present as amide or alkyl amide with 1 to 6 carbon atoms in the alkyl group or as diamide or as dialkyl amide with 1 to 6 carbon atoms in the alkyl groups.

The acyl groups with 1 to 6 carbon atoms are especially the acetyl group, the propionyl group and the butyryl group, while the preferred alkyl groups of 1 to 6 carbon atoms are the methyl group, the ethyl group, the propyl group and the various butyl groups. Also, in the corresponding thymosin $\alpha_1$ fragments position 1 can be varied by a lysine residue instead of serine, and positions 24 and 25 by gamma-carboxyglutamic acid (Gla) instead of glutamic acid residues.

Characteristic features of the above-described fragments in accordance with the invention are summarized in the following table.

| Fragment | No. | A+ | B+ | Spectra |
|---|---|---|---|---|
| Lys (2-6) | Ia | 9 | 28 | NMR |
| (7-12) | II | 24 | 38 | NMR |
| (11-19) | III | — | 8 | NMR |
| (20-24) | IV | — | 23 | NMR |
| (25-28) | V | — | 21 | NMR |
| (20-28) | VI | 5 | 12 | NMR |
| (13-18) | VII | 9 | 24 | NMR |
| (7-28) | VIII | 3 | — | — |
| Ac (1-12) | IX | — | 21 | — |
| (20-23) Gla | IVa | — | 31 | NMR |

+$R_f \times 100$
Solvent A: Mixture of amyl alcohol, pyridine, methyl ethyl ketone, formic acid and water 40:28:11:5:15 (V/V)
Solvent B: Mixture of n-butanol, pyridine, glacial acetic acid and water 5:5:1:4 (V/V)

The spectra given in the above table are represented in FIGS. 3 to 10 of the drawing.

Also subject matter of the invention are the pharmaceutically acceptable salts of the above-specified fragments I to IX.

The thymosin $\alpha_1$ fragments of the invention can be prepared by the application of conventional methods of peptide synthesis, such as conventional synthesis in solution with maximum protection or minimum protection of the side chains, by solid-phase synthesis according to Merrifield wherein the peptide is built up on the polymeric carrier, or by the polymer reagent method wherein the peptide is passed over the polymer-bound activated amino acid to lengthen the chain.

In an especially preferred manner, however, the thymosin $\alpha_1$ fragments of the invention are formed by the process of the Applicant's prior patent application No. P 29 19 592.4. In this process the thymosin $\alpha_1$ fragments of the invention are built up by a step-wise sequential lengthening by the mixed anhydride method, wherein especially protective groups are used which have a tertiary carbon atom in the urethane grouping, such as the tertbutyloxycarbonyl group (abbreviated Boc), the $\alpha,\alpha$-dimethyl-3,5-dimethoxybenzyloxycarbonyl group (Ddz) and the 2-(p-biphenyl)-propyl-2-oxycarbonyl group (Bpoc), which suppress secondary reactions by steric interference, and make it possible to use repeatedly great excesses of the mixed anhydride.

Figure 2:
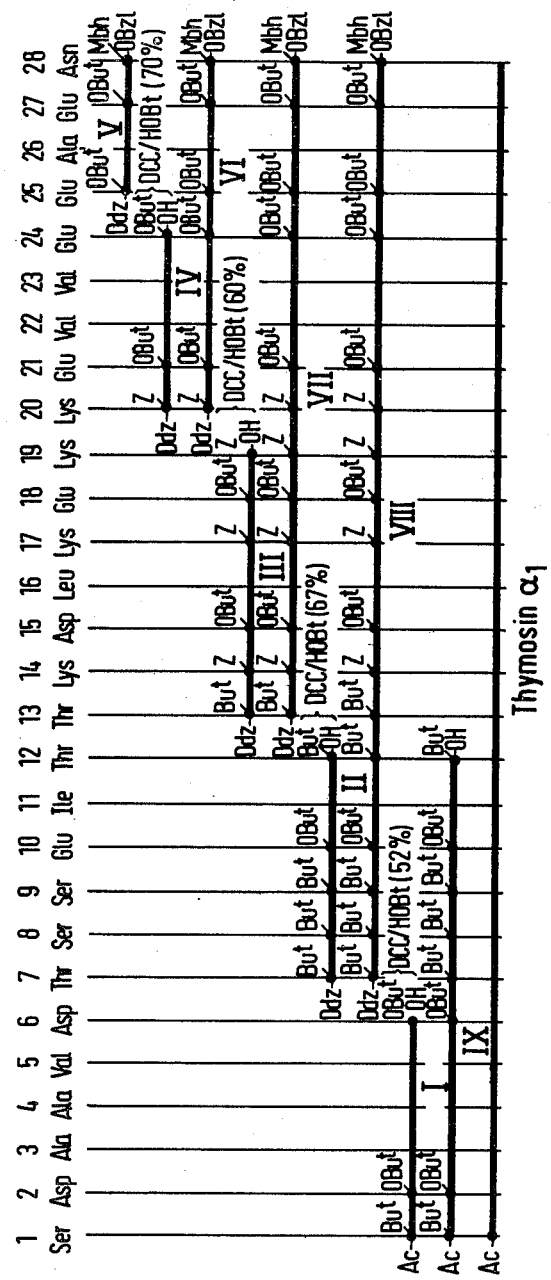
Figure 3:
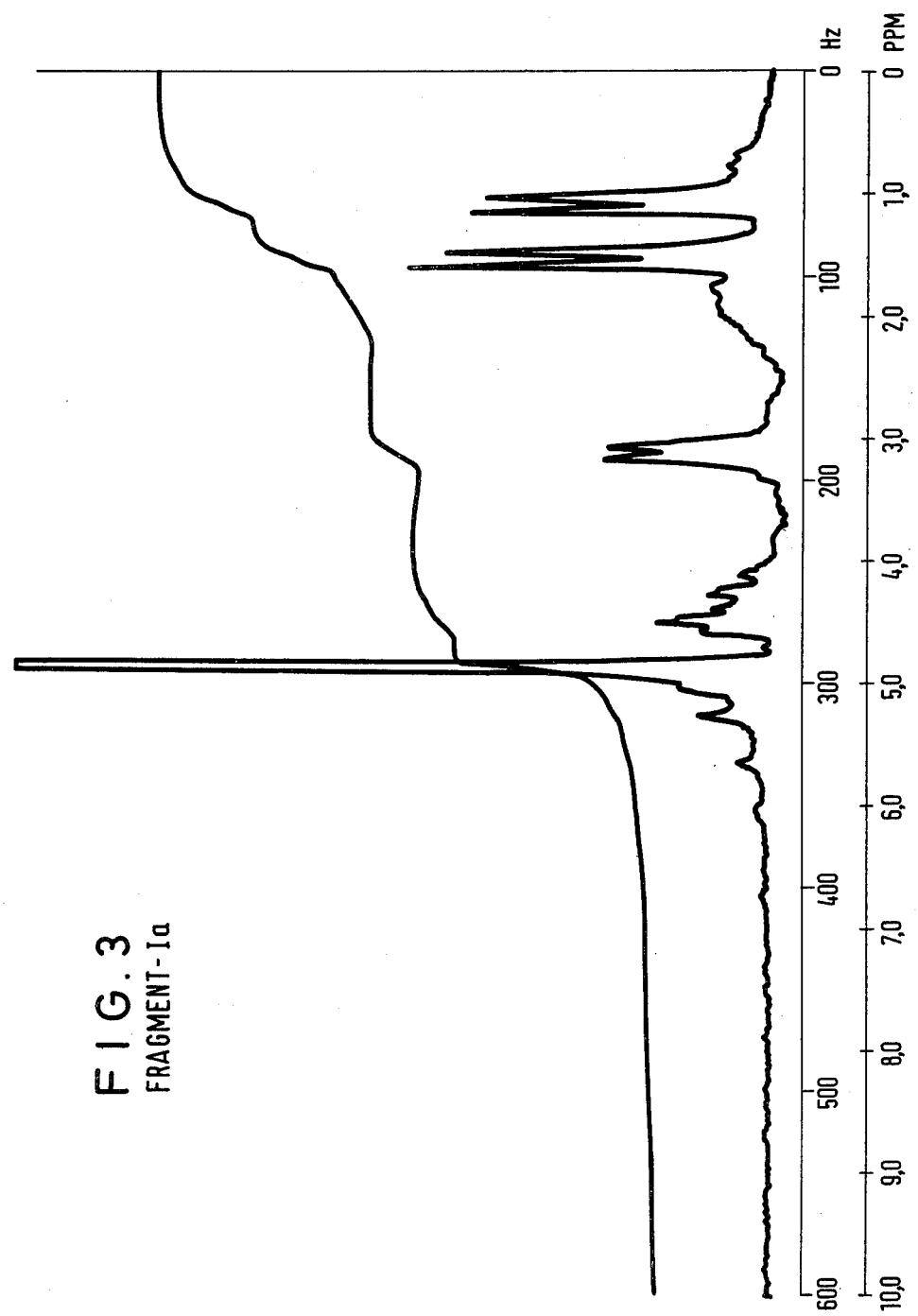
Figure 4:
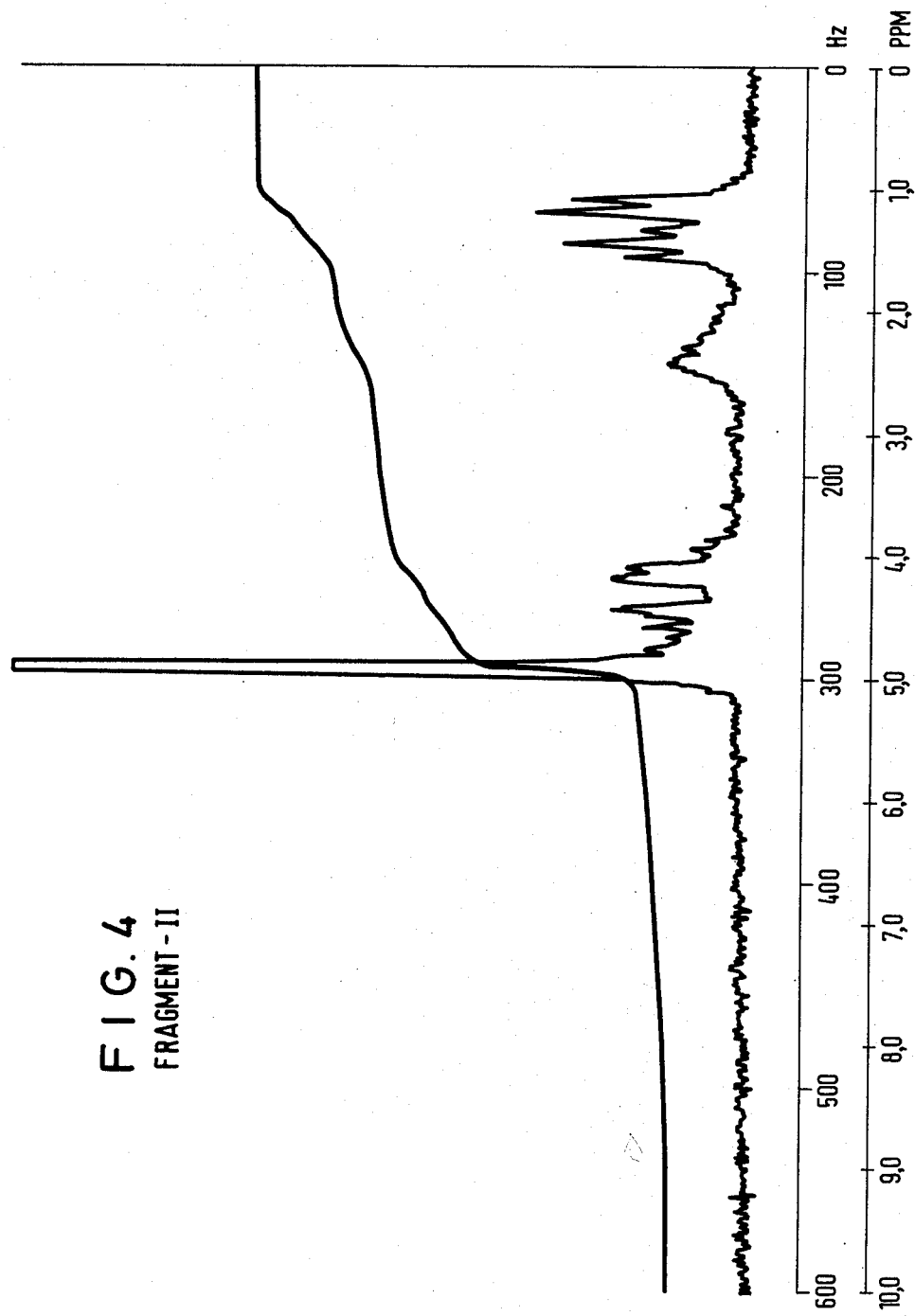
Figure 5:
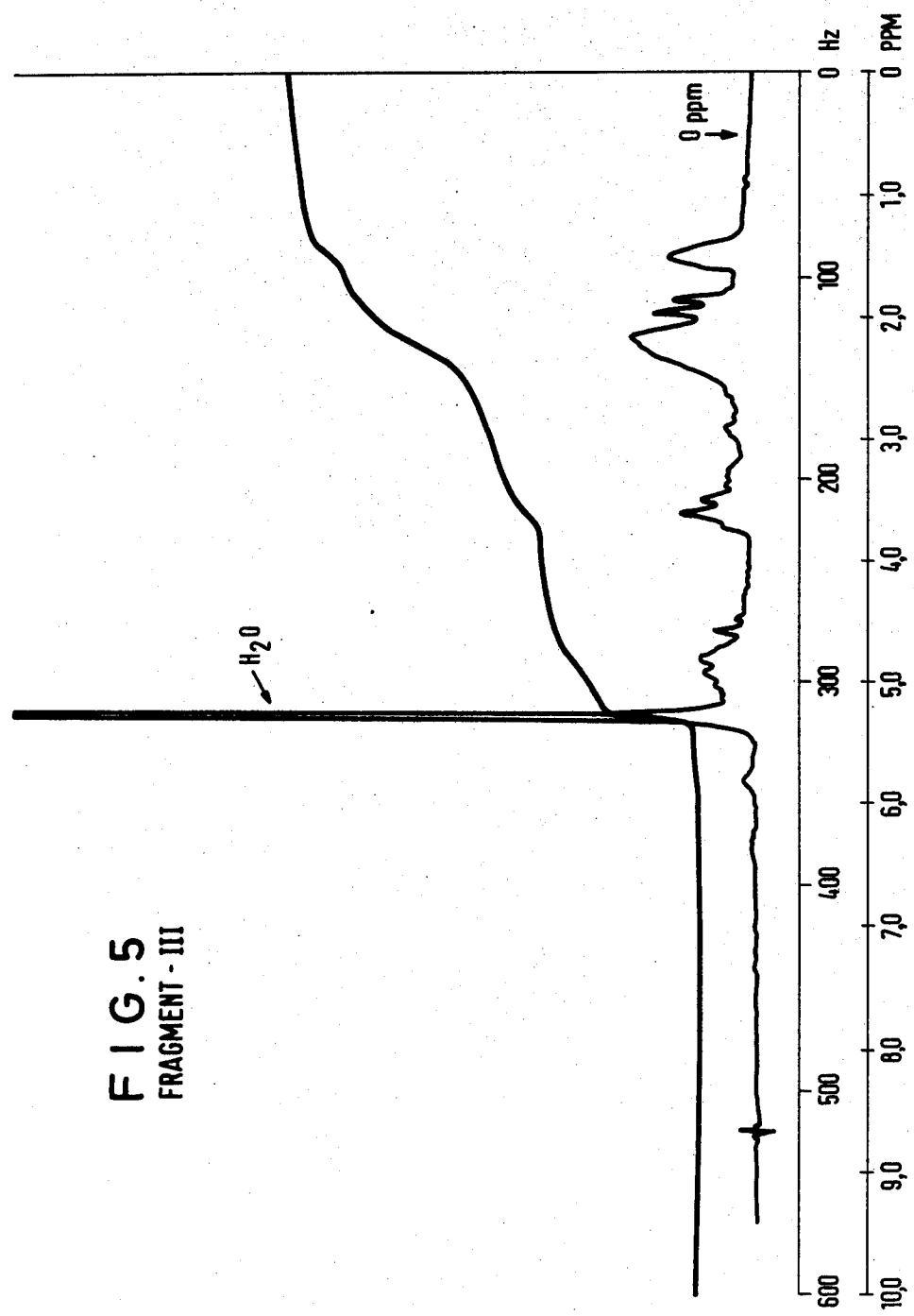
Figure 6:
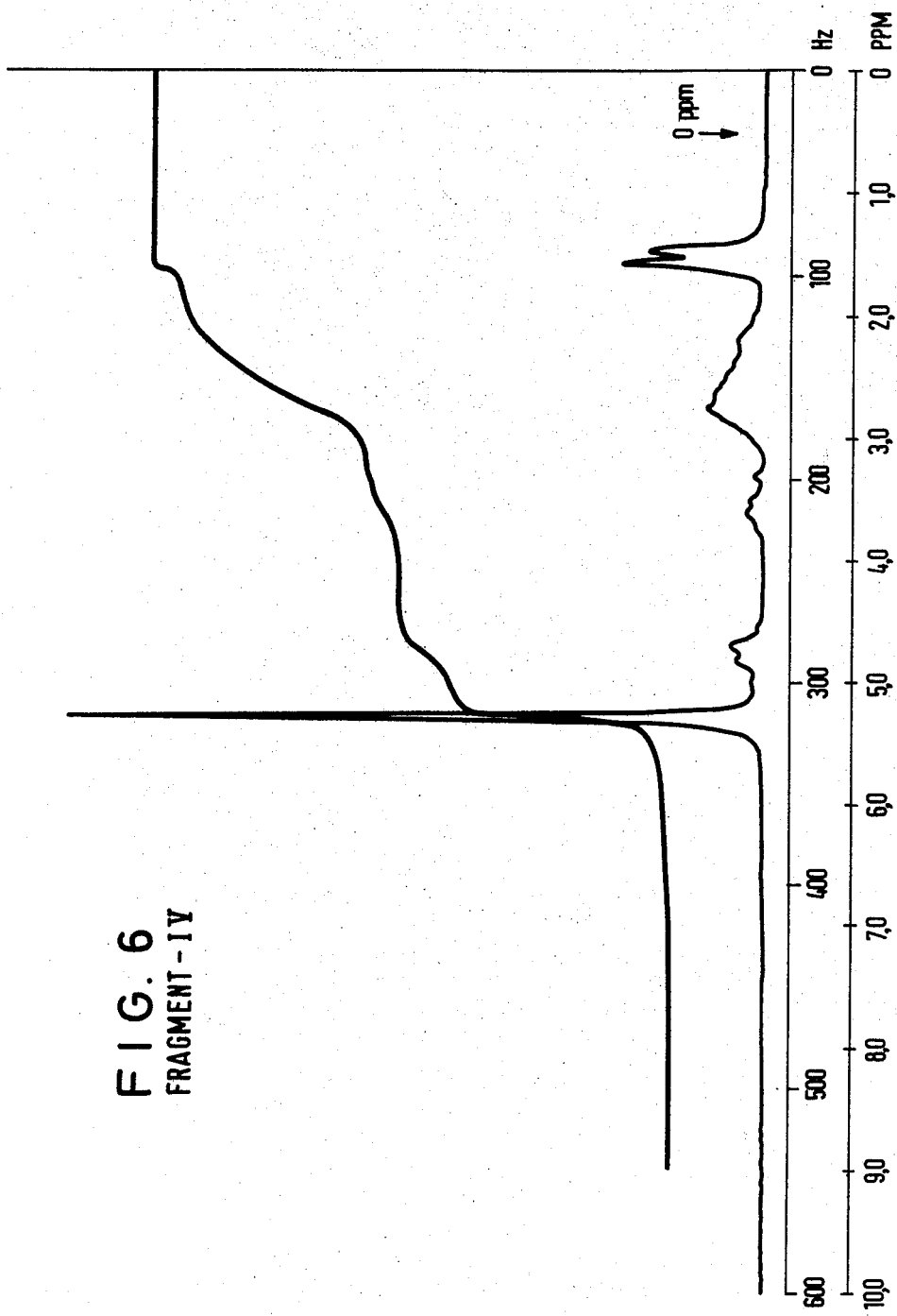
Figure 7:
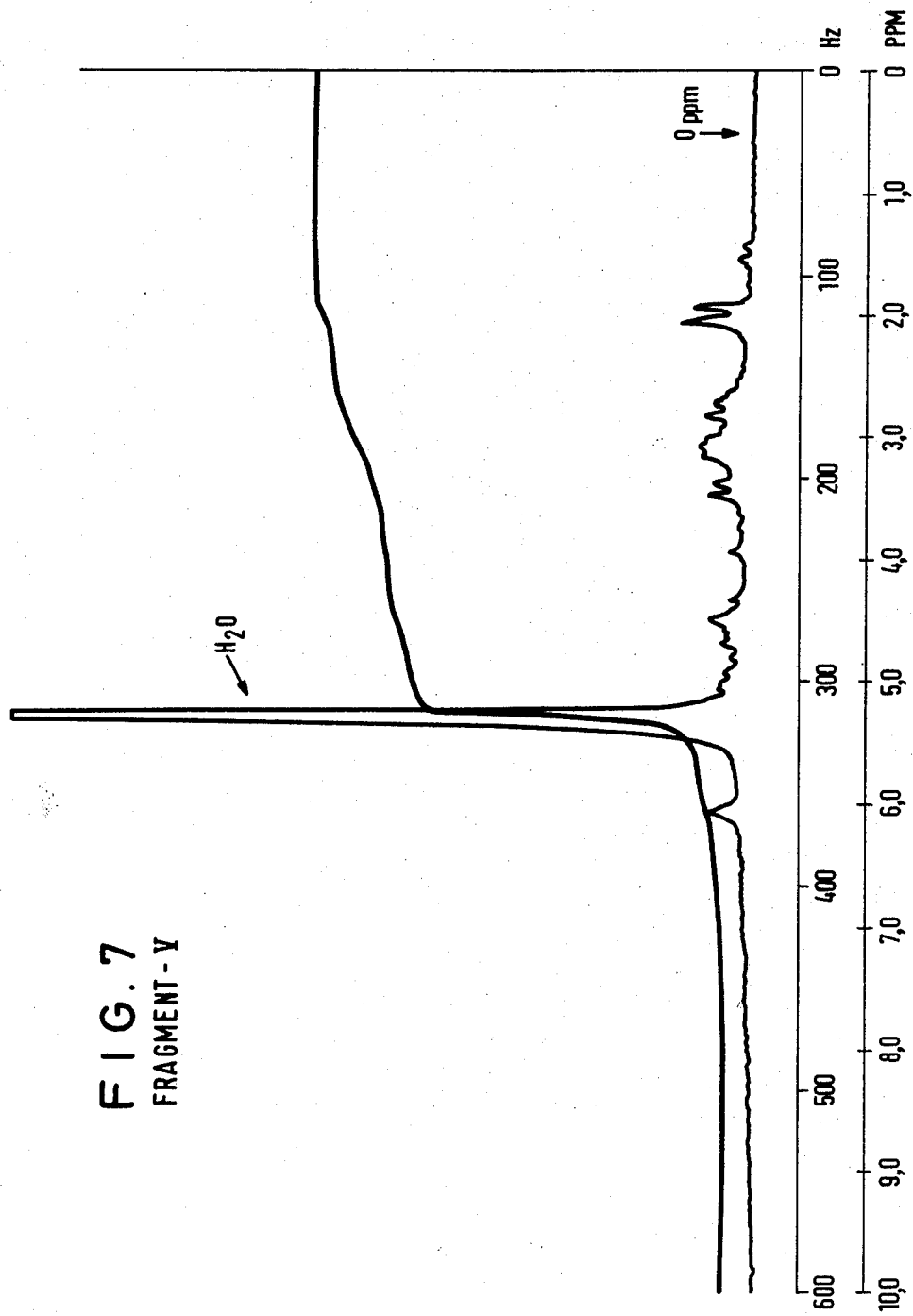
Figure 8:
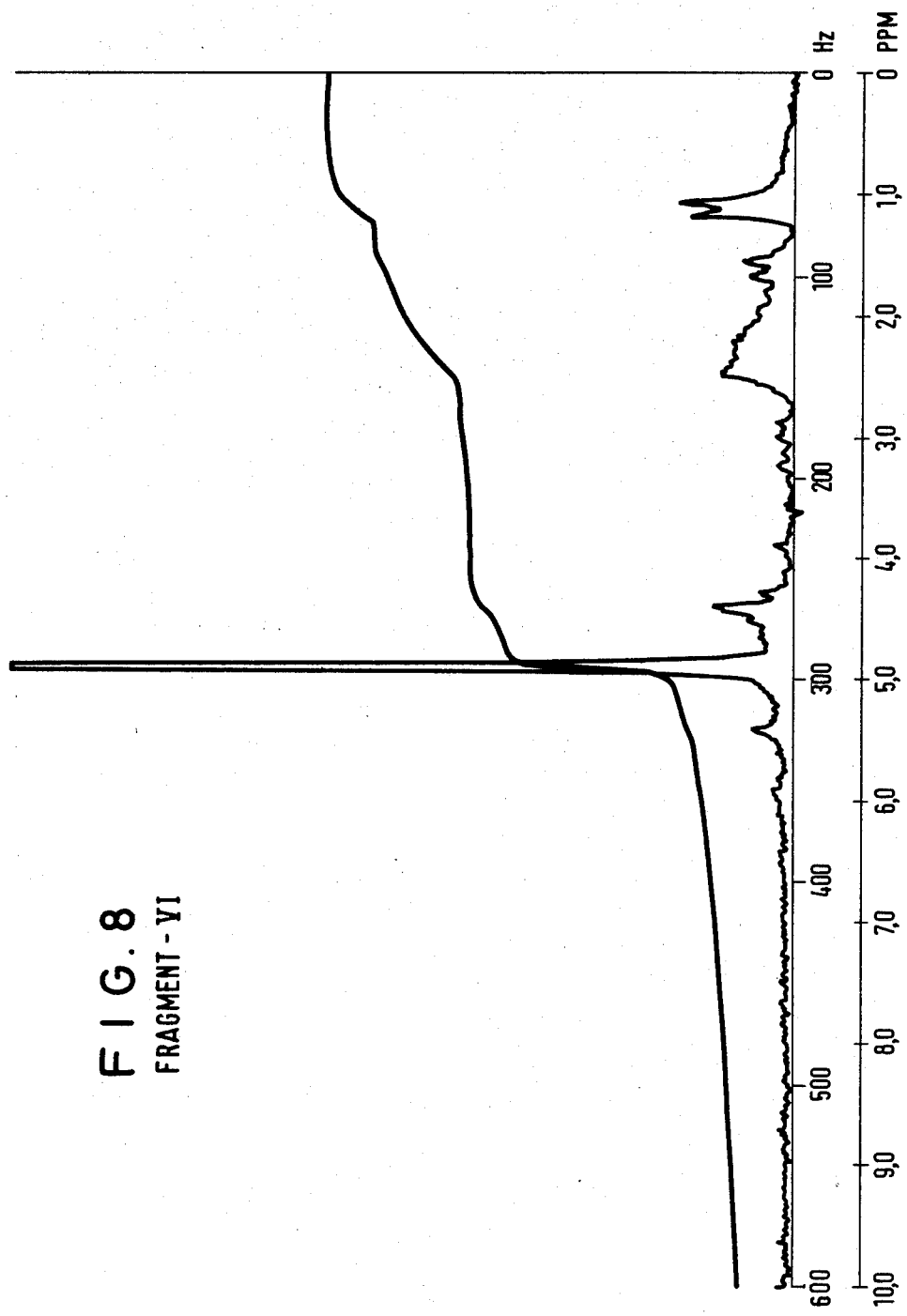
Figure 9:
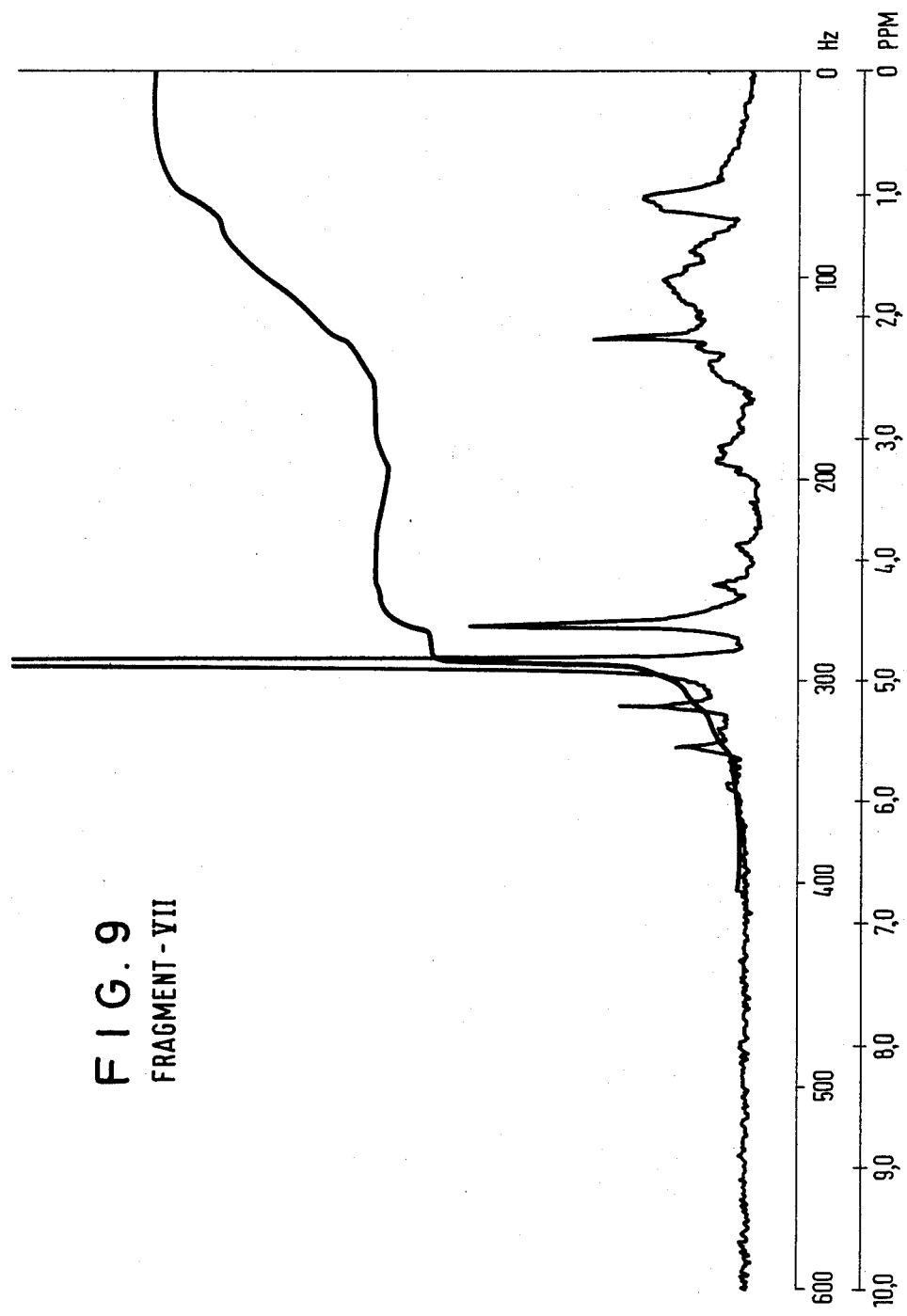
Figure 10:
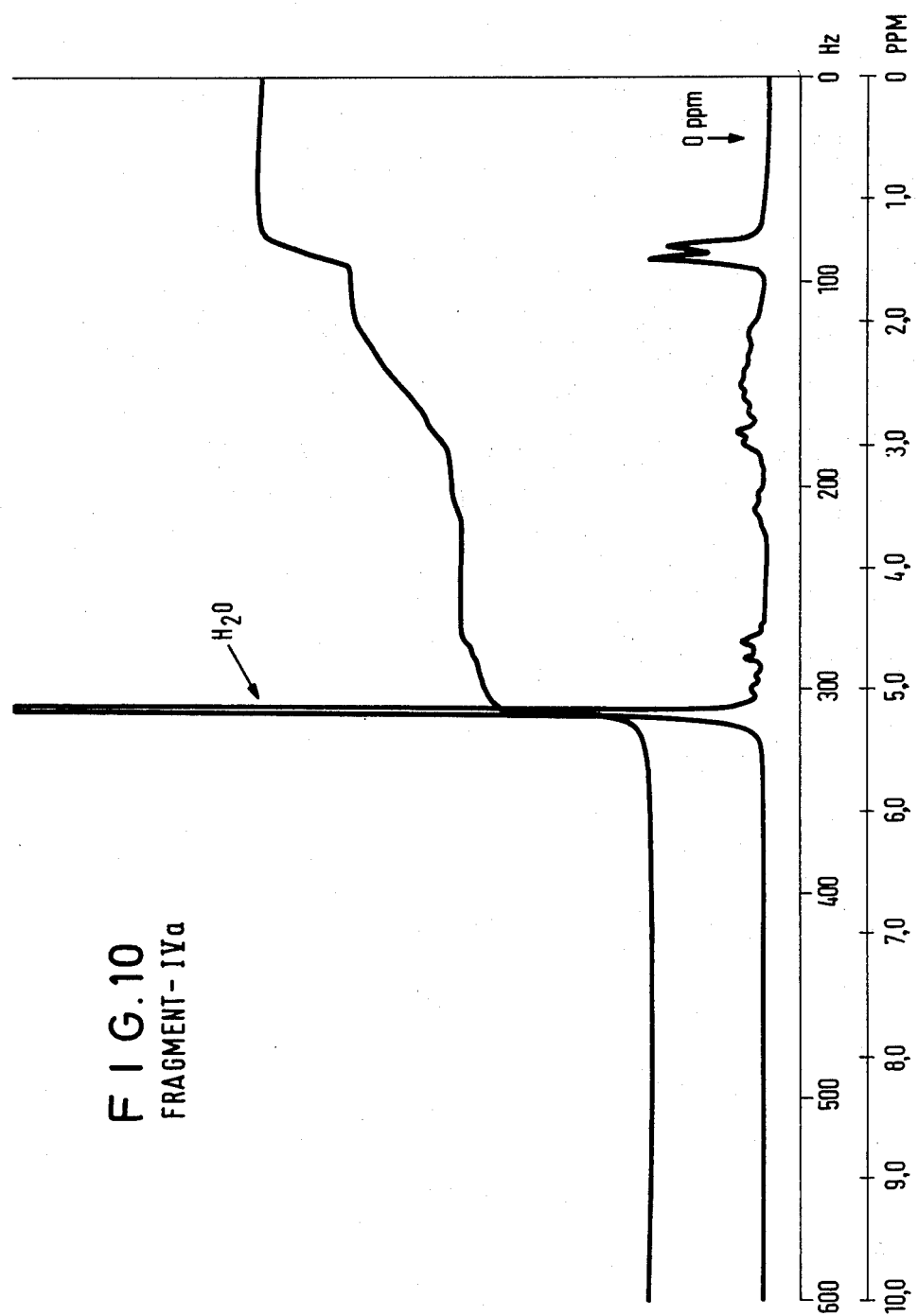

In the appended drawings:

FIG. 1 is a schematic representation of the primary structure of thymosin $\alpha_1$, FIG. 2 is a schematic representation of the fragments of the invention as obtainable pursuant to the synthesis of thymosin $\alpha_1$ in accordance with patent application No. P 29 19 592.4 (co-pending U.S. application of the same applicants claiming priority of the above German Application), and FIGS. 3 to 10 are NMR spectra of the fragments Ia, II, III, IV, V, VI, VII and IVa.

The invention will now be explained further with reference to the appended FIG. 2, which is a schematic representation of the thymosin $\alpha_1$ fragments of the invention with the protective groups used in their preparation. The abbreviations used therein and in the examples correspond to the proposals of the IUPAC-IUP (J. Biol. Chem. 247 (1972) 977-983). These are:

Ddz: $\alpha,\alpha$-dimethyl-3,5-dimethoxybenzyloxycarbonyl,
Z: Benzyloxycarbonyl,
Ac: Acetyl,
OBu$^t$: tertbutyl ester p0 MbH: 4,4'-dimethyloxybenzohydryl,
Me: methyl,
Obzl: benzyl ester, and
Bu$^t$: tertbutyl.

The following examples will elucidate the preparation of the thymosin $\alpha_1$ fragments of the invention and their pharmacological effectiveness.

The methods of preparation described in the following examples terminate in the protected thymosin $\alpha_1$ fragments, whose protective groups can be split off in the following manner:

Splitting Off The Protective Groups

An eight-fold to ten-fold excess of anhydrous trifluoroacetic acid in the form of a 5% solution in methylene chloride (absolute) is added to the Ddz-protected peptide ester and stirred for 15 to 30 minutes at room temperature. In the case of the longer peptides the time is to be extended. If the acid-labile 4,4'-dimethoxybenzohydryl group is contained in the sequence, the Ddz-protective group is split off with 2.5% or 1% trifluoroacetic acid for 30 to 60 minutes. To stop the reaction the solution is chilled to −15° C. and brought to a pH of 7.0 to 7.5 with the calculated amount of N-methylmorpholine (+10%).

Peptide methyl esters are dissolved in alcohol, dioxane, tetrahydrofuran or dimethylformamide in an ultrasonic bath with the addition of 20% of water, and is saponified therein with 2 equivalents of 1N NaOH. At the end of the reaction time, which is determined by thin-layer chromatography, the mixture is neutralized with acetic acid, concentrated in vacuo, and the concentrate is chromatographed in methanol on Sephadex LH20.

With trifluoroacetic acid in the form of a 50% solution in methylene chloride with the addition of anisole, the tertbutyl ester residues as well as the tertbutyl ether groups are primarily split off, and then, finally, the 4,4'-dimethoxybenzhydryl protective group is dissolved out with 95% trifluoroacetic acid/anisole. If the fragments contain benzyloxycarbonyl protective groups and/or benzyl esters, these are split off before the trifluoroacetic acid treatment by hydrogenation in alcoholic solution in the presence of palladium on charcoal in a conventional manner.

The thymosin $\alpha_1$ fragments of the invention can be transformed in a conventional manner, by the use of preferably pharacologically acceptable acids or bases, to the corresponding salts.

EXAMPLE 1

Thymosin $\alpha_1$ Fragment V

Preparation of Ddz-(25-28)-Obzl

Ddz-(28)-OBzl, Ddz-Asn(Mbh)-OBzl 3 ml of triethylamine (10% excess) and 3.48 g (=2.43 ml) of benzyl bromide are added to 11.6 g (20 mmol) of Ddz-Asn(MbH)-OH in 10 ml of dimethylformamide at 0° C. The solution is stirred overnight at room temperature and poured into 200 ml of ice water. The suspension is immediately neutralized with NaHCO$_3$ solution, the solid substance is dissolved with ethyl acetate, and the organic phase is washed with KHSO$_4$ solution (cold) and NaHCO$_3$ solution. If free acid is still found in 93:7 [sic], a silica gel column with CHCl$_3$/ethanol 94:6 as eluent is connected for the final purification. Yield 8.2 g=61%. For further data see Table I.

Ddz-(27-28)-OBzl, Ddz-Glu(OBu$^t$)-Asn(MbH)-OBzl 7 mmol of Ddz-Glu(OBu$^t$)-OH is reacted with 10 mmol of Asn(MbH)-OBzl to form the dipeptide in accordance with the general working procedure for mixed anhydride synthesis. After the conventional shake-out procedure, a chromatography is performed on a silica gel column with CHCl$_3$/ethanol 93:7. The dipeptide is then still contaminated with Ddz cleavage product, which does not, however, interfere with further synthesis operations. For information see Tables I and IX.

Ddz-(26-28)-OBzl, Ddz-Ala-Glu(OBu$^t$)-Asn(MbH)-OBzl 15 mmol of Ddz-Ala-OH is reacted as usual with 9.3 mmol of Ddz-(27-28)-OBzl to form the tripeptide, which is purified chromatographically on Sephadex LH20 with methanol and on silica gel with CHCl$_3$/ethanol 93:7. Yield 50%. For further data see Tables I and IX.

Ddz-(25-28)-OBzl, Ddz-Glu(OBu$^t$)-Ala-Glu(OBu$^t$)-Asn(Mbh)-IBzl (protected thymosin $\alpha_1$ fragment V)

The tetrapeptide is obtained pure by a standard method after chromatography on Sephadex LH20 with methanol. Yield 78%. The peptide is slightly soluble in pure methanol but after the addition of dimethylformamide it is easily soluble. The solubility in CHCl$_3$ is slight, but is good in a mixture of CHCl$_3$ and methanol. For further data see Tables I and IX.

The splitting off of the protective groups in the manner described above leads to the desired thymosin $\alpha_1$ fragment V.

EXAMPLE 2

Thymosin $\alpha_1$ Fragment IV

Preparation of Ddz-(20-24)-OMe (a) Ddz-(24)-OMe, Ddz-Glu(OBu$^t$)-OMe:

20 mmol of Ddz-Glu(OBu$^t$)-OH is dissolved in acetone and the equivalent amount of diazomethane (ether solution) is added. 100% yield of a yellowish oil, chromatographically uniform. For additional data see Table II.

(b) Ddz-(23-24)-OMe, Ddz-Val-Glu(OBu$^t$)-OMe 7.5 mmol of Ddz-Val-OH is reacted with 5 mmol of Ddz-Glu(OBu$^t$)-OMe to the dipeptide. Final purification on silica gel with CHCl$_3$/ethanol 93:7. The peptide still contains Ddz cleavage fragments which do not affect further synthesis steps. For information see Tables II and IX.

(c) Ddz-(22-24)-OMe, Ddz-Val-Val-Glu(OBu$^t$)-OMe

The tripeptide is obtained pure by a conventional method after chromatography through Sephadex LH 20 with methanol. It is easily soluble in methanol and CHCl$_3$. 60% yield of a colorless oil. For further data see Tables II and IX.

(d) Ddz-(21-24)-OMe, Ddz-Glu(OBu$^t$)-Val-Val-Glu(OBu$^t$)-OMe 6 mmol of Ddz-Glu(OBu$^t$)-OH is reacted to the tetrapeptide as usual with 2.98 mmol of Ddz-(22-24)-OMe. It is placed on a Sephadex LH 20/methanol column to obtain the product as a colorless glass in a 94% yield. The tetrapeptide dissolves easily in CHCl$_3$, methanol, dimethylformamide and dioxane. It is uniform in thin-layer chromatography in 93:7. 7:1 and 85:10:5, and it has the usual violet color with ninhydrin. For further data see Tables II and IX.

(e) Ddz-(20-24)-OMe, Ddz-Lys(Z)-Glu(OBu$^t$)-Val-Val-Glu(OBu$^t$)-OMe (protected fragment IV)

9 mmol of Ddz-Lys(Z)-OH is reacted to the pentapeptide as usual with 2.43 mmol of Ddz-(21-24)-OMe. After the shake-out procedure it is purified chromatographically on a methanol/Sephadex LH 20 column, to obtain the product as a colorless glass in a 99% yield. For further information see Tables II and IX.

By conventional splitting off of the protective groups the desired thymosin $\alpha_1$ fragment IV is obtained.

EXAMPLE 3

Thymosin $\alpha_1$ Fragment III

Preparation of Ddz-(13-19-OMe (a) Ddz-(19)-OMe, Ddz-Lys(Z)-OMe 20 mmol of Ddz-Lys(Z)-OH is dissolved in tetrahydrofuran and the equivalent amount of ethereal diazomethane solution is added. The amino acid residue is obtained in a 95% yield as a yellowish oil after shaking with NaHCO$_3$ solution. Crystallization from the common solvents was unsuccessful. For further data see Table III.

(b) Ddz-(18-19)-OMe, Ddz-Glu(OBu$^t$)-Lys(Z)-OMe

The dipeptide is prepared by conventional method. The peptide is obtained as a yellowish oil contaminated with small amounts of Ddz cleavage fragments. For data see Tables III and X.

(c) Ddz-(17-19)-OMe, Ddz-Lys(Z)-Glu(OBu$^t$)-Lys(Z)-OMe.

The synthesis of the tripeptide is accomplished in a normal manner by the conventional method. 20 mmol of Ddz-Lys(Z)-OH is reacted with 10 mmol of Ddz-(18–19)-OMe. After the acid and alkaline extraction, the chromatography is performed first on silica gel with $CHCl_3$/ethanol 97:3, then on Sephadex LH 20 with methanol. Yield: 86% of a colorless, deliquescent foam. For further data see Tables III and X.

(d) Ddz-(16–19)-OMe, Ddz-Leu-Lys(Z)-Glu(OBu$^t$)-Lys(Z)-OMe

The tetrapeptide is prepared by a conventional method. After chromatography on LH 20/methanol, 4.1 g of a white, amorphous solid can be isolated in a 77% yield. The peptide is easily soluble in methanol and $CHCl_3$. For further data see Tables III and X.

(e) Ddz-(15–19)-OMe, Ddz-Asp(OBu$^t$)-Leu-Lys(Z)-Glu(OBu$^t$)-Lys(Z)-OMe

It is necessary to modify the general working procedure for the synthesis of the pentapeptide. The mixed anhydride synthesis is performed in the usual stoichometry (9.5 mmol of Ddz-Asp(OBu$^t$)-OH and 3.7 mmol of tetrapeptide) in a three-necked flask with a powerful stirrer. After the carboxyl component and the amine component are combined, the methylene chloride solution gels spontaneously at $-15°$ C. Liquefaction can be achieved by the addition of 40 to 60 ml of dimethylformamide. After 4 to 6 hours of reaction time, another 100 to 200 ml of dimethylformamide is added and the methyl chloride is cautiously removed by evaporation. The remaining dimethylformamide solution is slowly stirred into five times the volume of ice cold NaCl solution, and the white, flocculent precipitate is removed by suction filtering. After washing with water, repeating the precipitation and drying, the peptide is obtained in an 84% yield. Ddz cleavage residues can be washed out with ether.

The peptide is very slightly soluble in methanol, $CH_2Cl_2$, $CHCl_3$ and dioxane. A suspension can be prepared in 1,1-dichloroethane. The peptide is soluble without problems in 5% trifluoroacetic acid/$CH_2Cl_2$. For further data see Tables III and X.

(f) Ddz-(14–19)-OMe, Ddz-Lys(Z)-Asp(OBu$^6$)-Leu-Lys(Z)-Glu-(OBu$^t$)-Lys(Z)-OMe 3.5 mmol of Ddz-Lys(Z)-OH and 1.74 mmol of Ddz-(15–19)-OMe can be reacted to the hexapeptide without further solubility problems. After chromatography on Sephadex LH 20/methanol, a glassy solid is obtained in a yield of about 100%. The product is easily soluble in methanol, especially after the addition of di-methylformamide. For further data see Tables III and X.

(g) Ddz-(13–19)-OMe, Ddz-Thr(Bu$^t$)-Lys(Z)-Asp(OBu$^t$)-Leu-Lys(Z)-Glu(OBu$^t$)-Lys(Z)-OMe (protected fragment III). 11.4 mmol of Ddz-Thr(Bu$^t$)-OH is reacted with 5 mmol of Ddz-(14–19)-OMe, being careful that the heptapeptide remains dissolved for the acid-/alkaline extraction in $CH_2Cl_2$, that is, that the usual change of solvent is eliminated. The peptide is only slightly soluble in ethyl acetate, methanol and dimethylformamide, but easily soluble in $CH_2Cl_2$ and $CHCl_3$. Chromatographic purification is performed on silica gel and $CHCl_3$/ethanol 98:2 as eluent, after which the heptapeptide is obtained in a 56% yield. It strikingly turns yellowish red with ninhydrin. For further data see Tables III and X.

(h) By splitting off the protective groups the desired thymosin $\alpha_1$ fragment III is obtained.

EXAMPLE 4

Thymosin $\alpha_1$ Fragment II

Preparation of Ddz-(7–12)-OBzl (a) Ddz-(12)-OBzl, Ddz-Thr(Bu$^t$)-OBzl 20 mmol of Ddz-Thr(Bu$^t$)-OH are esterified with benzyl bromide as specified for Ddz-Asn(Mbh)-OBzl. By extraction with $KHSO_4$ solution and $KHCO_3$ solution a chromatographically uniform oil can be obtained in a 73% yield. For further data see Table IV.

(b) Ddz-(11–12)-OBzl, Ddz-Ile-Thr(Bu$^t$)-OBzl

After splitting off Ddz from 10 mmol of Ddz-Thr(Bu$^t$)-OBzl, the dipeptide is prepared by a conventional method from 15 mmol of Ddz-Ile-OH. This is chromatographed on silica gel with chloroform/ethanol 98:2, and crystallized from $CCl_4$/n-heptane. 5.1 g of fine, white needles (=8.47 mmol, 85%) was thus obtained. For further data see Table IV.

(c) Ddz-(10–12)-OBzl, Ddz-Glu(OBu$^t$)-Ile-Thr(Bu$^t$)-OBzl 16 mmol of Ddz-Glu(OBu$^t$)-OH is reacted with 8 mmol of Ddz-(11–12)-OBzl in the usual manner to form the tripeptide. After acid and alkaline extraction, chromatography is performed with methanol on LH 20. Yield 89%. For further data see Table IV.

(d) Ddz-(9–12)-OBzl, Ddz-Ser(Bu$^t$)-Glu(OBu$^t$)-Ile-Thr(Bu$^t$)-OBzl

The tripeptide is prepared conventionally from 7 mmol of Ddz-(10–12)-OBzl with 14 mmol of Ddz-Ser(Bu$^t$)-OH. After acid and alkaline extraction, purification is performed on a silica gel column ($CHCl_3$/ethanol) 98:2). 5.3 g of a white amorphous substance is obtained (5.8 mmol, 83% having a melting range from 172° to 177° C. For further data see Table IV.

(e) Ddz-(8–12)-OBzl, Ddz-Ser(Bu$^t$)-Ser(Bu$^t$)-Glu(OBu$^t$)-Ile-Thr(Bu$^t$)-OBzl

The pentapeptide is obtained conventionally from 11.6 mmol of Ddz-Ser(Bu$^t$)-OH and 5.8 mmol of Ddz-(19–12)-OBzl. After acid and alkaline extraction, the product is dissolved in methanol/dimethylformamide 8:2 and placed on a Sephadex LH 20/methanol column. The peptide, which is poorly soluble in methanol, spontaneously crystallizes in the eluate. 4.7 g of white needles are obtained, which is a 78% yield. For further data see Tables IV and X.

(f) Ddz-(7–12)-OBzl, Ddz-Thr(Bu$^t$)-Ser(Bu$^t$)-Ser(Bu$^t$)-Glu-(OBu$^t$)-Ile-Thr(Bu$^t$)-OBzl (protected fragment II)

The hexapeptide is obtained conventionally from 6.2 mmol of Ddz-Thr(Bu$^t$)-OH and 3.5 mmol of Ddz-(8–12)-OBzl. After acid and alkaline extraction, the peptide, which is poorly soluble in methanol, is dissolved in dimethylformamide/methanol and placed on an LH 20 column and eluted with methanol. 4.0 g of a glassy, amorphous substance, which is turned yellowish red by ninhydrin, yield=97%. The peptide is soluble in benzene, $CH_2Cl_2$, $CHCl_3$ and dimethylformamide. For further data see Tables IV and X.

(g) In like manner one obtains Ddz-(7–12)-OMe, Ddz-Thr(Bu$^t$)-Ser(Bu$^t$)-Ser(Bu$^t$)-Glu(OBu$^t$)-Ile-Thr(Bu$^t$)-OMe (protected fragment II)

The synthesis is performed in a manner entirely analogous to the preparation of the Ddz-(7–12) benzyl ester. All of the properties of the intermediate products can be seen in Table V and Table I, respectively.

(h) By splitting off the protective groups the desired fragment II of thymosin $\alpha_1$ is obtained.

EXAMPLE 5

Thymosin α₁ Fragment I

Preparation of Ac-(1–6)-OBzl (a) Ddz-(6)-OBzl, Ddz-Asp(OBu$^t$)-OBzl 20 mmol of Ddz-Asp(OBu$^t$)-OH is esterified with benzyl bromide in a manner similar to that specified for Ddz-(28)-OBzl. By extraction with KHSO₄ solution and KHCO₃ solution, a chromatographically uniform oil can be obtained in an 81% yield. For data see Table VI.

(b) Ac-(1)-OH, Ac-Ser(Bu$^t$)-OH

Ddz is split off with 5% trifluoroacetic acid from 20 mmol of Ddz-Ser(Bu$^t$)-OH, and the solvent is withdrawn in vacuo. The product is dissolved at 0° C. with 20 ml of 1N NaOH and transferred to a three-necked flask. 200 mmol (=15.6 g) of acetyl chloride, diluted 1:1 with dioxane, is added drop by drop on the pH-stat at pH 9, while maintaining the temperature at 0° to 4° C. Thirty minutes after the addition has been completed, about 50 ml of a dioxane/H₂O azeotrope is withdrawn in vacuo. The alkaline solution is extracted with ether, adjusted to pH 2 to 3 with KHSO₄ and washed again with ether. Finally the product is extracted from the aqueous phase with ethyl acetate. 3.6 g=96% is obtained of an amorphous substance which crystallizes in granular, colorless form from ethyl acetate in the refrigerator. For further data see Table VI.

(c) Ddz-(5–6)-OBzl, Ddz-Val-Asp(OBu$^t$)-OBzl 15 mmol of Ddz-Val-OH is reacted in a conventional manner with 11.5 mmol of Ddz-Asp(OBu$^t$)-OBzl. The dipeptide is chromatographed on silica gel with CHCl₃/ethanol 99:1. For data see Tables VI and X.

(d) Ddz-(4–6)-OBzl, Ddz-Ala-Val-Asp(OBu$^6$)-OBzl 20 mmol of Ddz-Ala-OH is reacted with Ddz-(5–6)-OBzl to the peptide without difficulty. Chromatographic purification on Sephadex LH 20/methanol. For data see Tables VI and X.

(e) Ddz-(3–6)-OBzl, Ddz-Ala-Ala-Val-Asp(OBu$^t$)-OBzl

The tetrapeptide is prepared in a conventional manner from 17 mmol of Ddz-Ala-OH and 8.8 mmol of Ddz-(4–6)-OBzl. In the acid and alkaline extraction the peptide flocculates out of ethyl acetate, but can be kept in suspension. Gel chromatography (LH 20) does not show a chromatographically uniform product. Therefore another chromatography is performed on silica gel in CHCl₃/ethanol 99:1. 4.5 g of a colorless, amorphous product is obtained in a 70% yield. For further data see Tables VI and X.

(f) Ddz-(2–6)-OBzl, Ddz-Asp(OBu$^t$)-Ala-Ala-Val-Asp(OBu$^t$)-OBzl.

In the conventional reaction of 11.6 mmol of Ddz-Asp(OBu$^t$)-OH with 5.8 mmol of Ddz-(3–6)-OBzl, the poor solubility of the amine component in CH₂Cl₂ is striking. Peptide that has precipitated like a gel can be dissolved in dimethyl formamide after the Ddz removal and during the coupling. The crude pentapeptide is dissolved in methanol/dimethylformamide and chromatographed on LH 20, crystallizing from the fractions of the chromatography in fine white needles. Yield 85%. For data see Tables VI and X.

(g) Ac-(1–5)-OBzl, Ac-Ser(Bu$^t$)-Asp(OBu$^t$)-Ala-Ala-Val-Asp(OBu$^t$)-OBzl (protected fragment I)

2.8 mmol of Ac-Ser(Bu$^t$)-OH is reacted as usual with 1.4 mmol of Ddz-(2–6)-OBzl. After the reaction has ended and the CH₂Cl₂ has been withdrawn, the product is dissolved in 150 ml of dimethyl formamide and stirred into a 5% solution of NaHCO₃ saturated with NaCl. The precipitated product is suction filtered, washed with water and dried. It is dissolved in a little CHCl₃ and applied to a MERCK ready-prepared column. The column is eluted with alcohol-free CHCl₃ and, after the run, the front is developed with a linear gradient from CHCl₃ mixed with 0 to 10% of ethanol. 950 mg of a white, amorphous peptide is obtained. It is not easily soluble in CHCl₃, cannot be stained with ninhydrin, but reacts with "Chlor I/II." For data see Tables VI and X.

(h) Preparation of Ddz-(1–6)-OMe

The hexapeptide is prepared in a manner similar to that used in preparing Ac-(1–6)-OBzl.

Ddz-Ser(Bu$^t$)-Asp(OBu$^t$)-Ala-Ala-Val-Asp(OBu$^t$)-OMe.

The hexapeptide dissolves well in methanol/dimethylformamide. It can be chromatographed easily on Sephadex LH 20. Its solubility in CHCl₃, tetrahydrofuran and dioxane is moderately good, but definitely better than that of the acetyl peptide.

The fragment Ddz-(1–6)-OBzl described hereinbelow has the same properties also.

(i) Preparation of Ddz-(1–6)-OBzl

The hexapeptide is prepared in a manner similar to the method used in preparing Ac-(1–6)-OBzl, using Ddz-Ser(Bu$^t$) instead of Ac-Ser(Bu$^t$).

(j) Preparation of Ddz-Lys(Z)-(2–6)-OBzl; (protected fragment Ia)

7 mmol of Ddz-Lys(Z)OH and 3.1 mmol of Ddz-(2–6)-OBzl are reacted to the hexapeptide as usual. After chromatography on Sephadex LH 20/methanol, the uniform end product is obtained. For data see Tables VI and XI.

(k) By splitting off the protective groups the desired fragment I or Ia, Lys-(2–6)-OH, is obtained from the products designated under (i) and (j).

EXAMPLE 6

Thymosin α₁ Fragment VII

Synthesis of the fragment Ddz-(13–28)-OBzl (a) Saponification of Ddz-(20–24)-OMe, Ddz-Lys(Z)-Glu(OBu$^t$)-Val-Val-Glu(OBu$^t$)-OMe 1 mmol (1.1 g) of Ddz-(20–24)-OMe is dissolved in 20 ml of aqueous 80% dioxane (concentration 50 mmol). An ultrasonic bath is helpful for this purpose. Then 2 ml (2 mmol) of 1N NaOH is added and the mixture is stirred for one hour. The reaction time is determined by preliminary experiment. After stopping the saponification with 1 mmol of acetic acid, a part of the dioxane is withdrawn with a rotary evaporator and the residue is separated on a Sephadex LH 20/methanol column into a peptide peak and a salt peak. The peptide peak contains the chromatographically pure peptide acid in a 76% yield. For further data see Tables VII and XI.

(b) Fragment Condensation to Ddz-(20–28)-OBzl (protected fragment VI)

The protective group is split off from 895 mg (=0.86 mmol, 15% excess) of Ddz-(25–28)-OBzl in a 45-minute reaction with an 8-fold excess of 2.5% trifluoroacetic acid in CH₂Cl₂. The stopping of the reaction and the neutralization (pH 7.5) is performed with 1.0 ml of N-methylmorpholine. The solvent is concentrated in vacuo.

800 mg (0.75 mmol) of Ddz-(20–24)-OH is dissolved in 15.2 ml of dimethylformamide (final concentration 50 mM); the amine component is added and the mixture is cooled to 0° C. Then 1.52 mmol (=313 mg, 2 equivalents) of dicyclohexylcarbodiimide and 349 mg (2.28 mmol, 3 equivalents) of 1-hydroxybenzotriazole. H₂O is added. The clear solution is stirred for one hour at 0° C., and then warmed slowly to room temperature. After another hour, dicyclohexylurea suddenly precipitates in microcrystalline threads. After a total of 24 hours of reaction time, the mixture is chilled to 0° C., centrifuged free of dicyclohexylurea, and precipitated in 50 ml of 5% NaHCO₃ solution; the precipitate is washed with ice water and dried.

The crude substance (0.7 mmol=93%) is dissolved in CHCl₃ and placed on a MERCK prepared column K 60, Size C, which is balanced with CHCl₃. A low gradient of CHCl₃ is applied against CHCl₃/ethanol 90:10. 1.1 g (=70%) of pure nonapeptide is obtained. For further data see Tables VIII and XI.

(c) Saponification of Ddz-(13-19)-OMe, Ddz-Thr(Buᵗ)-Lys(Z)-Asp(OBuᵗ)-Leu-Lys(Z)-Glu(OBuᵗ)-Lys(Z)-OMe 0.7 mmol of Ddz-(13-19)-OMe (=1.2 g) is dissolved with 9 ml of tetrahydrofuran and 4 ml of methanol under the action of ultrasound; then 2 ml of water is added (final concentration 47 mM). After the addition of 1.5 ml of 1N NaOH (1.4 mmol), the saponification is performed for 25 minutes. The reaction time is determined by preliminary experiment. The reaction is stopped with 0.7 mmol of acetic acid. After concentration, chromatography is performed on Sephadex LH 20/methanol.

For further data see Tables VII and XI.

(d) Fragment condensation to Ddz-(13-28)-OBzl (protected fragment VII)

The Ddz protective group is split off from 583 mg (=0.3 mmol) of Ddz-(20-28)-OBzl in a 45-minute reaction with a 10-fold excess of 2.5% trifluoroacetic acid in CH₂Cl₂. The stopping of the reaction and the neutralization are performed with 0.33 ml of N-methylmorpholine (pH 7.5.) The solvent is withdrawn in vacuo.

663 mg (=0.4 mmol, 1.33 equivalents) of Ddz-(13-19)-OH is dissolved in 12 ml of dimethyl formamide (final concentration 25 mM); the amine component is added, and the mixture is chilled to 0° C. Then 165 mg (0.8 mmol) of dicyclohexylcarbodiimide and 184 mg (=1.2 mmol) of 1-hydroxybenzotriazole.H₂O is added. The clear solution, again adjusted to pH 7.5 with N-methylmorpholine, is stirred for one hour aat 0° C., then slowly warmed up to room temperature. After another 1.5 to 2 hours, dicyclohexylurea suddenly precipitates in microcrystalline threads. After a total of 66 hours (24 hours in a second batch), the temperature is lowered to 0° C., the dicyclohexylurea is centrifuged out, and chromatography is performed on a large LH 20/methanol column. From the first peptide-containing fractions a white, flocculent material precipitates, which is identified as hexadecapeptide. The second and third peaks of the separation contain unreacted carboxyl component or amine component.

The hexadecapeptide is obtained as a white powder which is slightly soluble in methanol, but easily soluble after the addition of dimethylformamide. Incipient decomposition appears at 230° C., which is complete at 260° C. For further data see Tables VIII and XI.

(e) By conventional splitting off of the protective groups, the desired fragment VII of thymosin α₁ is obtained.

EXAMPLE 7

Thymosin α₁ Fragment IX (a) Hydrogenation of Ac-(1-5)-OBzl, Ac-Ser(Buᵗ)-Asp(OBuᵗ)-Ala-Ala-Val-Asp(OBuᵗ)-OBzl.

500 mg of Ac-(1-6)-OBzl is steeped in 100 ml of isopropanol/10% acetic acid, and dissolved with 600 ml of isopropanol at 50° C. in the vibratory mixer. The hydrogenation is performed at room temperature in the vibratory mixer with 1 g of Pd/C in a stream of H₂. After 9 hours the catalyst is removed by a suction filter and the solvent is withdrawn in vacuo with the addition of toluene. The crude product in methanol with some dimethylformamide added is placed on an LH 20 column and chromatographed. Yield 300 mg=67%.

The hydrogenation can also be performed in 50 ml of 2,2,2-trifluoroethanol with 0.5 g of Pd/C, and the purification can also be performed on LH 20/2,2,2-trifluoroethanol. For analysis data see Tables VII and XI.

(b) Fragment Condensation to Ac-(1-12)-OBzl (protected fragment IX)

1.54 g (=1.3 mmol) of Ddz-(7-12)-OBzl is dissolved in 15 ml of CH₂Cl₂ and 0.77 ml of trifluoroacetic acid (8-fold excess, 5% solution) to split off the Ddz protective groups. After 15 minutes the mixture is neutralized (pH 7.5) with 1.4 ml of N-methylmorpholine (1.2 equivalents).

900 mg of Ac-(1-6)-OH (=1.17 mmol) is dissolved together with the amine component in 35 ml of dimethylformamide and 11 ml of N-methylmorpholine, and the mixture is cooled to 0° C. 2.34 mmol (=2 equivalents) of dicyclohexylcarbodiimide and 3.51 mmol (=3 equivalents) of 1-hydroxybenzotriazole.H₂O are added and stirred for one hour at 0° C. During the 60 hours of reaction time at room temperature, an increasing turbidity of the solution is observed, due to dodecapeptide precipitating in the manner of a gel. The solution is centrifuged, and the precipitate is washed twice with dimethylformamide and twice with water, and dried. 1.4 g of a white powder was obtained. This corresponds to 0.72 mmol, i.e., a yield of 61% of the theory.

The product is largely insoluble: CH₂Cl₂, CHCl₃, dioxane, tetrahydrofuran, methanol, dimethylformamide, N-methylpyrrolidone, hexamethylphosphoric acid triamide, tertbutanol, isoamyl alcohol, isopropanol, cyclohexane, cyclohexanone, and the addition of Ac-OH, ether, benzine and other solvents, all fail to dissolve the peptide. It is soluble only in 2,2,2-trifluoroethanol. For further data see Tables VIII and XI.

(c) Hydrogenation of Ac-(1-12)-OBzl 566 mg of Ac-(1-12)-OBzl is hydrogenated overnight with 100 mg of Pd/C in 60 ml of distilled trifluoroethanol.

Purification is performed on a MERCK prepared silica gel column with a gradient of CHCl₃/2,2,2-trifluoroethanol/acetic acid 85:10:5 after 2,2,2-trifluoroethanol/acetic acid 90:10. The substance elutes in a low peak towards the end of the gradient. For data see Tables VII and XI.

(d) By splitting off the protective groups the desired fragment IX of thymosin α₁ is obtained.

EXAMPLE 8

Thymosin α₁ Fragment VIII (a) Saponification of Ddz-(7-12)-OMe, Ddz-Thr(Buᵗ)-Ser-(Buᵗ)-Ser(Buᵗ)-Glu(OBuᵗ)-Ile-Thr(Buᵗ)-OMe 1.0 g (0.95 mmol) of Ddz-(7-12)-OMe is dissolved in 19 ml of dioxane and 2.5 ml of H$_2$O is added. If the substance precipitates, ultrasound treatment can be used to obtain an emulsion suitable for the saponification. The reaction is started with 0.5 ml of 1N NaOH. After 20 and 40 minutes, an additional 0.5 ml and 0.9 ml, respectively, of 1N NaOH is added. The reaction is stopped after one hour with 0.95 mmol of acetic acid (pH 7.5).

The solvent is withdrawn in vacuo, and the residue is dissolved in methanol and chromatographed on LH 20/methanol, unreacted peptide ester being eluted ahead of the main peak of the peptide acid. The substance (57% yield) is easily soluble in methanol, CHCl$_3$ and toluene/methanol. For additional data see Tables VII and XI.

(b) Condensation of Fragment to Ddz-(7-28)-OBzl (protected fragment VIII).

In a typical batch, the Ddz protective group is split off from 120 mg of Ddz-(13-28)-OBzl (36 μmol) in a one-hour reaction with a 20-fold excess of 2.5% (or 1%) trifluoroacetic acid in CH$_2$Cl$_2$. The stopping of the reaction and the neutralization (pH 7.5) are performed with N-methylmorpholine (microliter syringe). The solvent is withdrawn in vacuo.

77 mg (72 μmol, 2 equivalents) of Ddz-(7-12)-OH is dissolved in 1.5 ml of dimethylformamide, the amine component is added, and the mixture is cooled to 0° C. Then 16 mg (78.6 μmol, 2.2 equivalents) of dicyclohexylcarbodiimide and 24 mg (157 μmol, 4.4 equivalents) of 1-hydroxybenzotriazole. H$_2$O is added and the pH is adjusted to 7.5 with N-methylmorpholine (theoretically 6.4 equivalents. The clear solution is stirred overnight at 0° C. Precipitation of the dicyclohexylurea shows the progress of the reaction. The solution is kept for 10 more hours at about 20° C., chilled again to 0° C., and the dicyclohexylurea is removed by centrifugation. The supernatant fluid is dripped into 30 ml of ice-cold methanol, whereupon the crude 22-peptide precipitates. It is vacuum dried, dissolved in 2,2,2-trifluoroethanol, and chromatographically purified on a 2,2,2-trifluoroethanol/LH-20 column (0.6×240 cm) by re-chromatographing the first peak until uniformity is achieved.

By splitting off the protective groups in the conventional manner, the desired fragment VIII of thymosin α$_1$ is obtained.

The 22-peptide is obtained as a glassy solid, which is insoluble in methanol, soluble in dimethylformamide, and easily soluble in 2,2,2-trifluoroethanol. The yields amounts to 67%. For further data see Tables VIII and XI.

TABLE I

Thymosin α$_1$-Fragment V

| | Yield | Appearance | MP (°C.) | hRf I | hRf II | α$^{20}$ 578 nm | α$^{20}$ 365 nm | (g/100 ml) | Solvent |
|---|---|---|---|---|---|---|---|---|---|
| Ddz—(28)—OBzl | 61% | white amorphous | 136–138 | 49 | 92 | −4,4° | −12,3° | 1,145 | Methanol |
| Ddz—(27-28)—OBzl | 100% | yellow crystalline | 125–132 | 35 | 92 | −4,8° | −15,6° | 1,465 | Methanol |
| Ddz—(26-28)—OBzl | 50% | white foamy | | | | −23,8° | −80,3° | 1,333 | Methanol |
| Ddz—(25-28)—OBzl | 78% | white amorphous | 154–156 | 24 | 90 | −14,5° | −51,1° | 0,440 | Methanol/Dimethylformamide (8:2 v/v) |

I: 7:1,
II: 85:10:5

TABLE II

Thymosin α$_1$-Fragment IV

| | Yield | Appearance | hRf I | hRf II | α$^{20}$ 578 nm | α$^{20}$ 365 nm | c(g/100 ml) | Solvent |
|---|---|---|---|---|---|---|---|---|
| Ddz—(24)—OMe | 100% | colorless oil | 57 | 92 | | | | |
| Ddz—(23-24)—OMe | 100% | oil | 47 | 92 | | | | |
| Ddz—(22-24)—OMe | 60% | colorless oil | 28 | 92 | | | | |
| Ddz—(21-24)—OMe | 94% | colorless foamy | 22 | 88 | | | | |
| Ddz—(20-24)—OMe | 99% | colorless glass | 05 | 92 | −44,5° | −155,9° | 0,53 | Methanol |

I: 7:1;
II: 85:10:5

TABLE III

Thymosin α$_1$-Fragment III

| | Yield % | Appearance | MP (°C.) | hRf I | hRf II | hRf III | hRf IV | α$^{20}$ 578 nm | α$^{20}$ 365 nm | c(g/100 ml) | Solvent |
|---|---|---|---|---|---|---|---|---|---|---|---|
| Ddz—(19)—OMe | 95 | yellowish oil | — | 45 | | 92 | | −6,2° | −16,4° | 1,000 | Methanol |
| Ddz—(18-19)—OMe | 100 | yellowish oil | — | 31 | | 90 | | −12,8° | | 1,000 | Methanol |
| Ddz—(17-19)—OMe | 86 | deliquescent foam | — | 15 | | 86 | 15 | −18,5° | −61,3° | 1,539 | Methanol |
| Ddz—(16-19)—OMe | 77 | white foamy | — | 21 | | 84 | | −29,7° | −100,0° | 0,740 | Methanol |
| Ddz—(15-19)—OMe | 84 | white amorphous | 184–185° (G.) | 16 | | 85 | | −21,8° | −70,0° | 0,370 | Dimethylformamid |
| Ddz—(14-19)—OMe | 100 | glass-like, colorless | — | 01 | | 92 | | −23,4° | −81,9° | 0,475 | Methanol |
| Ddz—(13-19)—OMe | 56 | glass-like, | — | 00 | 55 | 88 | | −24,5° | −87,2° | 0,375 | Methanol |

TABLE III-continued

| | | | | Thymosin α₁-Fragment III | | | | | | | |
|---|---|---|---|---|---|---|---|---|---|---|---|
| | | | | | hRf | | | $\alpha^{20}$ | | | |
| | Yield % | Appearance | MP (°C.) | I | II | III | IV | 578 nm | 365 nm | c(g/100 ml) | Solvent |
| | | colorless | | | | | | | | | |

I: 7:1
II: 93:7
III: 85:10:5
IV: 4:1:1

TABLE IV

| | | | | Thymosin α₁-Fragment II | | | | | | |
|---|---|---|---|---|---|---|---|---|---|---|
| | | | | | hRf | | $\alpha^{20}$ | | | |
| | Yield | Appearance | MP (°C.) | I | II | III | 578 nm | 365 nm | c(g/100 ml) | Solvent |
| Ddz—(12)—OBzl | 73% | colorless oil | — | 58 | | 59 | −17,5° | −53,5° | 2,017 | Methanol |
| Ddz—(11-12)—OBzl | 85% | fine needles | 116,5–117,5° | 57 | 83 | | −20,6° | −69,1° | 0,33 | Methanol |
| Ddz—(10-12)—OBzl | 89% | colorless foam | — | 38 | 92 | | | | | |
| Ddz—(9-12)—OBzl | 83% | white amorphous | 172–177° | 34 | 93 | | −4,3° | −19,8° | 0,515 | CH₂Cl₂ |
| Ddz—(8-12)—OBzl | 78% | white needles | 191–192° | 28 | 95 | | −2,2° | −16,5° | 0,87 | CH₂Cl₂ |
| Ddz—(7-12)—OBzl | 97% | glassy amorphous | | 17 | 92 | 58 | −5,1° | −6,9° | 0,505 | CH₂Cl₂ |

I: 7:1
II: 85:10:5
III: 93:7

TABLE V

| | | Thymosin α₁-Fragment II | | | | | |
|---|---|---|---|---|---|---|---|
| | | hRf | | $\alpha^{20}$ | | | |
| | Yield | I | II | 578 nm | 365 nm | c(g/100 ml) | Solvent |
| Ddz—(11-12)—OMe | 68,0% | 53 | 92 | −22,6° | −73,1° | 2 | Methanol |
| Ddz—(10-12)—OMe | 77,9% | 37 | 81 | −15,9° | −52,3° | 2 | Methanol |
| Ddz—(9-12)—OMe | 62,3% | 22 | 73 | −5,9° | −24,1° | 1 | Methanol |
| Ddz—(8-12)—OMe | 84,2% | 11 | 72 | −1,0° | −11,8° | 1 | Methanol |
| Ddz—(7-12)—OMe | 71,4% | 12 | 78 | −1,6° | −11,0° | 1 | Methanol |

I: 7:1
II: 93:7

TABLE VI

| | | | Thymosin α₁-Fragment I | | | | | | | | |
|---|---|---|---|---|---|---|---|---|---|---|---|
| | | | | hRf | | | | $\alpha^{20}$ | | | |
| | Yield | Appearance | I | II | III | IV | V | 578 nm | 365 nm | c(g/100 ml) | Solvent |
| Ddz—(6)—OBzl | 81% | colorless oil | 48 | | 40 | | | −19,8° | −70,7° | 1,388 | Methanol |
| Ac—(1)—OH | 96% | granular crystals | 07 | | | 71 | 38 | +39,2° | +133,3° | 0,354 | Ethyl acetate |
| Ddz—(5-6)—OBzl | 100% | yellowish oil | 58 | 92 | | | | −6,5° | −23,7° | 8,44 | Methanol |
| Ddz—(4-6)—OBzl | 76% | foam | 27 | 92 | | | | −47,4° | −171,2° | 0,515 | Methanol |
| Ddz—(3-6)—OBzl | 70% | colorless amorph | 24 | 78 | | | | −54,6° | −193,4° | 0,71 | Methanol |
| Ddz—(2-6)—OBzl | 85% | needles | 05 | 92 | | | | −24,6° | −97,7° | 0,435 | CH₂Cl₂ |
| Ac—(1-6)—OBzl | 78% | white foamy | 00 | 63 | 35 | | | −34,0° | −145,5° | 0,2 | Dimethylsulfoxide/Methanol |
| Ddz—(1-6)—OBzl | 84% | colorless amorpho | 04 | 90 | 47 | | | −31,0° | −142,0° | 0,5 | CH₂Cl₂ |
| Ddz—Lys(Z)—(2-6)—OBzl | 100% | colorless amorpho | 16 | 79 | | | | — | — | — | — |

I: 7:1
II: 85:10:5
III: 93:7
IV: 4:1:1
V: sec.-butanol/3% ammonia solution (100:44)

TABLE VII

| | | Thymosin α₁-Fragments I–IV and IX in the form of the peptide acids | | | | | | | | | |
|---|---|---|---|---|---|---|---|---|---|---|---|
| Frag- | | | | | | hRf | | $\alpha^{20}$ | | | |
| ment | | Yield | Appearance | MP (°C.) | I | II | III | 578 nm | 365 nm | c(g/100 ml) | Solvent |
| IV | Ddz—(20-24)—OH | 76% | glass-like | — | | 0 | 57 | | | | |
| III | Ddz—(13-19)—OH | 86% | white powder | 180–182 (Z) | 80¹ | 0 | 56 | −24,5° | −87,2° | 0,375 | Methanol |
| II | Ddz—(7-12)—OH | 57% | white powder | — | | 0 | 74 | −18,0° | −46,7° | 0,15 | Methanol |
| I | Ac—(1-6)—OH | 67% | white amorph. | 219–221° (Z) | | 0 | 22 | −47,1° | −190,0° | 0,014 | 2,2,2-trifluoro- |

TABLE VII-continued

Thymosin $\alpha_1$-Fragments I–IV and IX in the form of the peptide acids

| Frag-ment | | Yield | Appearance | MP (°C.) | hRf I | II | III | $\alpha^{20}$ 578 nm | 365 nm | c(g/100 ml) | Solvent |
|---|---|---|---|---|---|---|---|---|---|---|---|
| IX | Ac—(1-12)—OH | 85% | colorless glass | — | 0 | 25[2] | | −33,3° | −98,3° | 0,06 | ethanol |

I: 7:1
II: 93:7
III: 85:10:5
[1]4:1:1
[2]CHCl$_3$:2,2,2-trifluoroethanol/acetic acid

TABLE VIII

Thymosin $\alpha_1$-Fragments VI–IX

| Frag-ment | | Yield | Appearance | MP (°C.) | hRf I | II | III | $\alpha^{20}$ 578 nm | 365 nm | c(g/100 ml) | Solvent |
|---|---|---|---|---|---|---|---|---|---|---|---|
| VI | Ddz—(20-28)—OBzl | 70% | glass-like | 252° (Z) | 25 | 72 | | +13,1° | +29,4° | 0,435 | CHCl$_3$ |
| VII | Ddz—(13-28)—OBzl | 60% | white powder | 260° (Z) | 00 | 60 | 88 | −8,1° | −49,8° | 0,235 | CHCl$_3$/Methanol(8:2) |
| VIII | Ddz—(7-28)—OBzl | 67% | glass-like | — | | 50 | | −9,7° | −25,2°[1] | 2,593 | 2,2,2-trifluoroethanol |
| IX | Ac—(1-12)—OBzl | 61% | white powder | 263° (Z) | 34 | 77 | | −28,7° | −116,2° | 0,16 | 2,2,2-trifluoroethanol |

I: 93:7
II: 85:10:5
III: 4:1:1
[1]436 nm

TABLE IX

Amino acid analysis of thymosin $\alpha_1$-Fragments IV and V

| Frag-ment | | Hydrolysis Method | Asp | Glu | Ala | Val | Lys |
|---|---|---|---|---|---|---|---|
| V | Ddz—(25-28)—OBzl | a | 1,00 (1) | 1,90 (2) | 1,20 (1) | | |
| IV | Ddz—(20-24)—OMe | a | | 1,82 (2) | | 2,00 (2) | 1,05 (1) |

Hydrolysis method: a = HCl/propionic acid 160° C. 45 to 60 minutes

TABLE X

Amino acid analysis of Thymosin $\alpha_1$-Fragments I to III

| Frag-ment | | Hydrolysis Method | Asp | Thr | Ser | Glu | Ala | Val | Ile | Leu | Lys |
|---|---|---|---|---|---|---|---|---|---|---|---|
| III | Ddz—(13-19)—OMe | a | 0,96 (1) | 0,6 (1) | | 1,05 (1) | | | | 1,00 (1) | 2,75 (3) |
| II | Ddz—(7-12)—OBzl | b | | 1,82 (2) | 1,96 (2) | 1,08 (1) | | | 1,00 (1) | | |
| I | Ac—(1-6)—OBzl | b | 1,97 (2) | | 0,99 (1) | | 1,95 (2) | 1,00 (1) | | | |

Hydrolysis method:
a = HCl/propionic acid 160° C., 45 to 60 minutes
b = 6 n HCl 110° C., 18 to 24 hours

TABLE XI

Amino acid analysis of Thymosin $\alpha_1$-Fragments I to IX

| Frag-ment | | Hydrolysis Method | Asp | Thr | Ser | Glu | Ala | Val | Ile | Leu | Lys |
|---|---|---|---|---|---|---|---|---|---|---|---|
| V | Ddz—(25-28)—OBzl | a | 1,00 (1) | | | 1,90 (2) | 1,20 (1) | | | | |
| IV | Ddz—(20-24)—OH | a | | | | 1,82 (2) | | 2,00 (2) | | | 1,05 (1) |
| VI | Ddz—(20-28)—OBzl | b | 1,70 (1) | | | 4,3 (4) | 1,00 (1) | 1,36 (2) | | | 1,00 (1) |
| III | Ddz—(13-19)—OH | b | 1,12 (1) | 0,85 (1) | | 1,02 (1) | | | | 1,00 (1) | 2,75 (3) |
| VII | Ddz—(13-28)—OBzl | b | 1,94 (2) | 0,7 (1) | | 4,44 (5) | 0,71 (1) | 1,44 (2) | | 1,00 (1) | 3,76 (4) |
| II | Ddz—(7-12)—OMe | a | | 1,52 (2) | 1,38 (2) | 0,77 (1) | | | 1,00 (1) | | |
| II | Ddz—(7-12)—OH | b | | 1,75 (2) | 1,78 (2) | 1,16 (1) | | | 1,00 (1) | | |
| VIII | Ddz—(7-28)—OBzl | a | 2,09 (2) | 2,56 (3) | 1,07 (1) | 5,22 (6) | 0,78 (1) | 1,44 (2) | 0,85 (1) | 1,15 (1) | 3,91 (4) |
| I | Ac—(1-6)—OH | b | 1,84 (2) | | 0,91 (1) | | 1,97 (2) | 1,00 (1) | | | |
| IX | Ac—(1-12)—OBzl | b | 2,08 (2) | 1,87 (2) | 2,5 (3) | 0,56 (1) | 2,42 (2) | 1,00 (1) | 0,96 (1) | | |
| IX | Ac—(1-12)—OH | b | 2,12 (2) | 1,77 (2) | 2,45 (3) | 1,00 (1) | 2,12 (2) | 1,00 (1) | 1,10 (1) | | |
| Ia | Ddz—Lys—(2-6)—OBzl | a | 2,10 (2) | | | | 1,92 (2) | 1,00 (1) | | | 1,03 (1) |
| IVa | Ddz—(20-23)—Gla—OMe | a | | | | 2,11 (2) | | 2,00 (2) | | | 1,02 (1) |
| Va | Ddz—Gla—(25-28)—OBzl | a | 0,87 (1) | | | 2,09 (2) | 1,00 (1) | | | | |
| VIa | Ddz—(20-23—Gla$_2$—25-28)—OBzl | a | 1,11 (1) | | | 4,23 (4) | 1,00 (1) | 1,79 (2) | | | 0,98 (1) |

Hydrolysis method:
a = HCl/propionic acid 160° C., 45 to 60 minutes
b = 6 n HCl 110° C., 18 to 24 hours

EXAMPLE 9

In order to prove the immunostimulant and immunoregulating properties of the thymosin $\alpha_1$ fragments of the invention, immunological-pharmacological tests were performed.

The immunological test methods used were the E-rosette test according to Wara, Ammann et al. (N.Y. Acad. Sci. 249 (1975) 308 and N. Engl. J. Med. 292 (1975) 70) and the method of mixed lymphocyte culture, both methods involving additional inhibition of cellular RNS polymerase by alpha-amanitin. The E-rosette test is based on the fact that the percentage of E-rosette forming cells in peripheral human blood is a measure of the content of fully mature T-cells, which form with sheep's red blood cells characteristic aggregates which can be counted under the microscope. Experiments by Wara, Ammann et al (loc. cit.) have shown that in patients with thymus hypoplasia an increase from 20% to 45% can be achieved in the E-rosette formation, provided that an optimally active thymosin preparation is added. The normal level of E-rosette formation in the healthy human subject is 56%.

For the performance of the E-rosette test, peripheral human lymphocytes are isolated by a gradient centrifugation. Their RNS polymerase is blocked by alpha-amanitin. Then red blood cells from sheep and thymosin or a thymosin $\alpha_1$ fragment is added, which removes the alpha-amanitin blockage of the E-rosette formation, so that the normal level of the cell aggregate formation, which is 56%, can be achieved. This value is taken as 100% in a relative numerical scale, and after the alpha-amanitin blockage it is taken to be 0%; see Table XII.

The test in mixed lymphocyte cultures is based on the fact that T-cells are made to proliferate by stimulation with allogenic antigens. For the performance of the test, the lymphocytes of donor A ("responder") are incubated with those of donor B ("stimulator") for 4 to 5 days. Then $^3$H-thymidin is added and the rate of proliferation is measured on the basis of the increasing radioactivity of the cell culture due to the installation of the radioactive material. Since both populations A and B might be made to proliferate, resulting in an unclear effect, population B is blocked with mitomycin C in all metabolical activities. This test is routinely used before organ transplants to determine the immunological compatibility of donor and receiver tissues.

The results obtained in these pharmacological studies are given in the following Tables XII and XIII.

TABLE XII

Examples of the stimulation of human peripheral lymphocytes with thymosin $\alpha_1$ fragments in the E-rosette test after the cells are blocked with $\alpha$-amanitin (E-rosette number being then 0%; The normal level without any addition = 100%)

| Fragment | Ia | II | III | IV | V | VI | VII | IX | Thymosin | (synthetic) |
|---|---|---|---|---|---|---|---|---|---|---|
| E-rosette number (%) | 93 | 29 | 29 | 45 | 42 | 16 | 41 | 40 | 100 | |
| Optimum concentr. ($\mu$M) | 16 | 80 | 80 | 83 | 113 | 10 | 6 | 4 | 1.6 | |

TABLE XIII

Examples of the stimulation of human peripheral lymphocytes by thymosin $\alpha_1$ fragments in the test with mixed lymphocyte cultures, with and without blockage by $\alpha$-amanitin.
(1 $\mu$g thymosin $\alpha_1$ fragment per ml of cell culture; 1 $\mu$g of $\alpha$-amanitin per ml of cell culture (+) = stimulation
(−) = inhibition (%) of the culture by addition of thymosin $\alpha_1$ fragments. The reaction of the mixed lymphocyte culture without such addition is taken as 0%)

| | Fragment | | | | | | |
|---|---|---|---|---|---|---|---|
| | Ia | II | III | IV | V | VI | IX |
| Cell pairs | | | | | | | |
| AB | −8 | — | −64 | −53 | +223 | +153 | −74 |
| CD | −73 | −53 | −13 | +37 | +45 | +57 | −63 |
| BA | −15 | −18 | −12 | +565 | +791 | +1136 | — |
| DC | −31 | +30 | +12 | +2 | +37 | ±0 | −77 |
| Cell pairs* | | | | | | | |
| AB | −10 | −11 | −44 | −87 | −47 | +279 | −30 |
| CD | −53 | −98 | −20 | +35 | — | +83 | +63 |
| BA | — | −80 | +6 | −97 | −94 | −96 | −78 |
| DC | −7 | +20 | +80 | +100 | — | +160 | +60 |

*Cultures blocked with $\alpha$-amanitin

From the above Tables XII and XIII is immediately apparent that the thymosin $\alpha_1$ fragments of the invention, as shown by the Examples in Tables XII and XIII, exercise a very pronounced immunological action which enables them to be used in human therapy and in veterinary medicine.

If the immunological activities of the fragments, as shown in the above example, are compared with those of the parent substance, totally synthetic thymosin $\alpha_1$ (shown in Table XIV for the E-rosette test and in Table XV for the mixed lymphocyte culture), it can be concluded that all of the fragments studied have a pronounced action on the differentiating mechanism and on the maturation of thymus-related lymphocytes to immune-competent T-cells, as well as in their proliferation process.

Comparisons in detail of the immunological activities of the fragments with thymosin $\alpha_1$ clearly show that mechanisms of T-cell activation which express themselves in the E-rosette test are more strongly stimulated by N-terminal thymosin $\alpha_1$ fragments (VII, IX) than by the C-terminal fragments IV, V and VI. Here a special position is assumed by the especially active, unnatural fragment Ia, which, with its additional basic function (lysine) apparently exercises an effect on T-lymphocytes, which in the case of the natural fragments is brought about only in combination with median sections of the sequence. These fragments, which are especially active in the E-rosette test, also display a surprisingly pronounced inhibiting action in the mixed lymphocyte culture (see Table XIII for fragments Ia and IX) on the opposite cell-bound antigenicity of lymphocytes from different donors. This finding can acquire considerable importance in transplantation practice due to the possibility of the preparation of medicaments having an immuno-suppressive action on the basis of small, easy-to-synthesize peptides.

On the basis of the comparisons of thymosin $\alpha_1$ with the fragments IV, V and VI, however, it can be concluded from both of the bioassays that the immunologically stimulative center of thymosin $\alpha_1$ is located in the C-terminal area. Special attention must be called to the easy-to-synthesize peptides Glu-Ala-Glu-Asn (fragment V) and Lys-Glu-Val-Val-Glu (fragment IV), which show activity in the E-rosette test only at a relatively high dosage, but develop a very considerable stimulation of T-cell proliferation in the mixed lymphocyte culture.

This is because, when there is a lack of immune-competent T-cells (T-lymphocytes), the immunological recognition (cell-bound antibody formation) and defense of abnormal body cells is reduced. Cellular abnormalities may be due to virus infections, biological aging processes (cellular error) and various forms of development of cancer.

The results presented indicate that those fragments of thymosin $\alpha_1$ which display activities equivalent to or more powerful than the parent substance ought to be especially suitable for the preparation of medicaments against immunological deficiency diseases, senilities and virus infections, but above all against various forms of cancer (leukemia, pulmonary metastases).

TABLE XIV

Data on a comparison of synthetic thymosin $\alpha_1$ with a natural polypeptide prepared from thymus glands, in the E-rosette test with inhibition by $\alpha$-amanitin.

| Normal cell population: | 64%[a] | E-rosettes |
| Inhibited with $\alpha$-amanitin: | 25%[a] | E-rosettes |
| Thymus polypeptide[b] | | Synthetic thymosin $\alpha_1$[c] |
| μg per culture (%) | | μg per culture (%)[d] |
| 6.25 | 10 | 5.00 | 33 |
| 3.12 | 67 | 2.50 | 57 |

TABLE XIV-continued

Data on a comparison of synthetic thymosin $\alpha_1$ with a natural polypeptide prepared from thymus glands, in the E-rosette test with inhibition by $\alpha$-amanitin.

| Normal cell population: | 64%[a] | E-rosettes |
| Inhibited with $\alpha$-amanitin: | 25%[a] | E-rosettes |
| Thymus polypeptide[b] | | Synthetic thymosin $\alpha_1$[c] |
| μg per culture (%) | | μg per culture (%)[d] |
| 1.25 | 100 | 1.00 | 64 |
| 0.62 | 62 | 0.50 | 100 |
| 0.31 | 6 | 0.25 | 39 |

[a]Absolute value
[b]Isolated from thymus glands
[c]Analytically pure
[d]Relative number of the E-rosettes produced by stimulation with thymus peptides after their previous inhibition with $\alpha$-amanitin, from peripheral human lymphocytes.

TABLE XV

The stimulation by synthetic thymosin $\alpha_1$ of an allogenic mixed culture from peripheral human lymphocytes (stimulator cells blocked with mitomycin)

| Cell pairs | (%) (a) | Stimulation (c) (b) |
|---|---|---|
| AB | +20 | +86 |
| AD | +4 | +37 |
| DB | +27 | +1550 |
| BA | +27 | +47 |
| BD | +45 | +51 |
| DA | +44 | ±0 |

(a) Culture not inhibited
(b) Culture inhibited with 1 microgram of $\alpha$-amanitin per ml of the cell suspension
(c) Culture stimulated by the addition of 1 microgram of thymosin $\alpha_1$ per ml of cell suspension; the lymphocyte stimulation in the culture without the addition of thymosin $\alpha_1$ was taken as 0%.

We claim:
1. The compound Glu-Ala-Glu-Asn-OH.

* * * * *